United States Patent [19]

Bommelaer et al.

[11] Patent Number: 5,264,207
[45] Date of Patent: Nov. 23, 1993

[54] PRODUCTS FOR CUTANEOUS APPLICATIONS WITH COSMETIC AND/OR THERAPEUTIC EFFECTS

[75] Inventors: Jean Bommelaer, Le Cannet; André Franco, Menton, both of, France; Jean Gueyne; Marie-Christine Seguin, both of Monte Carlo, Monaco

[73] Assignee: EXSYMOL S.A.M., Monaco

[21] Appl. No.: 554,025

[22] Filed: Jul. 17, 1990

[30] Foreign Application Priority Data

Jul. 18, 1989 [FR] France .................. 89 09603

[51] Int. Cl.$^5$ .................................. A61K 7/035
[52] U.S. Cl. ........................ 424/69; 514/443; 514/817; 514/823; 514/863; 514/873; 514/887
[58] Field of Search ............... 424/69; 514/817, 823, 514/863, 873, 887, 443

[56] References Cited

U.S. PATENT DOCUMENTS

| | | | |
|---|---|---|---|
| 4,242,250 | 12/1980 | Gagnon | 524/817 |
| 4,500,676 | 2/1985 | Balazs | 424/82 |
| 4,624,665 | 11/1986 | Nuwayser | 424/449 |
| 4,655,767 | 4/1987 | Woodard | 424/448 |
| 4,687,481 | 8/1987 | Nuwaysen | 424/449 |
| 4,725,279 | 2/1988 | Woodroof | 424/447 |
| 4,828,561 | 5/1989 | Woodroof | 424/422 |
| 4,834,978 | 5/1989 | Nuwaysen | 424/448 |
| 4,946,870 | 8/1990 | Partain, III | 424/443 |

Primary Examiner—Thurman K. Page
Assistant Examiner—Robert H. Harrison
Attorney, Agent, or Firm—Ostrolenk, Faber, Gerb & Soffen

[57] ABSTRACT

Products for cutaneous application with cosmetic and/or therapeutic effects, containing one or more active substances. This or these substances are carried by the microspheres of a polymer, dispersed in a liquid in which this polymer is not soluble.

15 Claims, No Drawings

PRODUCTS FOR CUTANEOUS APPLICATIONS WITH COSMETIC AND/OR THERAPEUTIC EFFECTS

The invention relates to new products for cutaneous application, likely to exert a cosmetic or therapeutic effect, or both a cosmetic and therapeutic effect, following a particular order in time. These products represent a marked advance in the field of action on or by the skin. In particular, they prevent overcharging with substances that are often of no use or even harmful, frequently the case with conventional treatments. An important advantage of the invention resides in the fact that it leads to chronobiological action, whose favorable effects have recently been recognized. According to recent studies, it appears that the effectiveness of a therapeutic agent depends on the precise time at which it is applied: it varies from one individual to another as a function of the daily physiological cycle of the person in question. The new products according to the invention are well-adapted to application allowing their effect in time to be determined in advance. A single application of such a product is enough to an ensure release of its effects at one or more moments during the day or night. Because of the particular properties of the carrier used for the active substances, a product according to the invention can be used in amounts less than those required in the case of usual products, in particular lotions, creams, solutions, powders, etc.

The products according to the invention, which contain one or more active substances carried by the microspheres of a polymer, dispersed in a liquid in which this polymer is not soluble, are characterized in that they include at least two sets of microsphere-active substance releasing the active substance at different times.

The microspheres of the various polymers and the technique for their preparation are known and there is no need to describe them here. Descriptions of such products and the processes for their preparation can be found, for example, in patents FR 1 572 106 and 2 304 326, EP 0 064 967 or EP 0 274 961. However, they do not have the chronobiological properties of the products according to the present invention.

Although the invention can relate to microscopic spheres of varying dimensions, the size of such spheres preferably does not exceed 1000 nm, preferred sizes ranging from 50 to 500 nm or, even better, from 60 to 300 nm.

The optimum size of particles further depends on the kind of polymer constituting them.

Given the fineness of the microspheres used according to the invention, their specific area per unit weight is fairly substantial, thus leading to high adsorption, or electrostatic or covalent combination of the active substances of the particles contacted. This leads to the possibility, as mentioned above, of obtaining products that are much richer in active substances than conventional compositions which require high proportions of excipient, the first, and not least, disadvantage of which is blocking skin pores. As the active substance in the products according to the invention is bound to the microspheres, it is released progressively and, consequently, is not likely to lead to overcharging although it can still be applied in amounts that may be relatively high.

The microparticles suitable for application of the invention can be chosen from various microspheres of known polymers, solid or hollow, as long as they are insoluble in the carrier liquid used. The latter is most often water. Nonetheless, it can also be an organic liquid tolerated by the skin and by the organism such as, for example, a polyol such as glycol or glycerine, a polyol ether or ester, in particular a lipid, such as a biologically acceptable vegetable or animal oil.

The following microparticles of polymers are thus suitable for application according to the invention: polysaccharides, polyamides, polyalkylenes, polyarylalkylenes, polyalkylidenes, polysilicones and others. In each of the categories, a large number of derivatives and copolymers can also be used. For example, polysaccharides such as xanthan, scleroglucane, pectins, starches, celluloses, cyclodextrins and their derivatives such as amylose, amylopectin, carboxymethylcellulose, hydroxycellulose, alkylcelluloses, dextrin, etc. can also be used. Polysaccharides polymerized with proteins can be used when microencapsulation of active substances is required at the same time.

The following can be given as examples of polyarylalkylenes: polystyrene and especially its copolymers, particularly with ethylene esters, namely acrylates or methacrylates of various alkyls, hydroxyalkyls with methacryl- or acryl-amide. Similarly, vinyl resins are also suitable, for example, polyvinyl acetate and its copolymers with acrylates or methacrylates, etc.

Adsorption capacity and affinity for cosmetic or therapeutic active substances varies according to the kind of polymer making up the microspheres and the size of these microspheres. These properties are taken advantage of in the present invention to obtain products that are more or less charged with active substances, releasing the latter at more or less different times. Thus, according to a particular feature of the invention, products releasing active substances at different times are characterized by the joint presence of several kinds of microsphere having different sizes and/or derived from different polymers.

For example, a product which, applied in the morning, has to react at three different times during the day is comprised of an aqueous dispersion of three kinds of microsphere, 90 to 160 nm in diameter: 1° from polysiloxane 2° from polyadipamide 3° from styrene-methyl methacrylate copolymer (90/10).

In another variant of the invention, a cosmetic product to be progressively reacted on the skin at different times of the day, following a single application, comprises for example (as microspheres of a butyl methacrylate-methacrylamide 70/30) 1.1% in weight of these microspheres of which 32% have sizes ranging from 60 to 100 nm, 45% have sizes ranging from 150 to 250 nm and 23% have diameters ranging from 300 to 500 nm.

Another mode of application of the invention consists in a suspension of microspheres to which one or more active substances are bound by different binding forces. Thus, according to the invention, a suspension of the microscopic spheres of a polymer can be obtained onto which an active substance is adsorbed, another substance binding to the polymer by chemical bonds, with the possibility of a third substance binding to the spheres by electrostatic or ionic bonds.

With some active substances and with suitable polymers, the spheres according to the invention can absorb the substance, thus forming a sort of solid solution.

Because of this difference in bonding the times at which the substance(s) is released also vary, which produces a chronobiological effect on using the suspensions according to the invention.

It should be noted that, in the case of covalent bonds between the active substance and the microspheres of a polymer, these bonds are either direct or indirect. Indirect bonds require an intermediate molecule providing a bridge between the active substance and the polymer's functional groups. Such intermediate molecules can, depending on the case, be compounds containing two functional groups such as, for example, diacids, diamines, amino acids, dialdehydes such as glyoxal, gluteraldehyde, glyoxime, carbodiimides, etc. In this case, the process for preparing the aqueous or organic microsphere suspension generally includes the addition of an intermediate compound before the adjunction of the active substance that is to be fixed via this intermediate compound.

When the microspheres are hollow, they are, in conformity with the invention, both adsorbent and/or carriers of functional groups. They produce a chronobiological effect since one or more encapsulated active substances are released at different times by the hollows of the sphere via the adsorption forces and various chemical and physicochemical bonds between the substance and the polymer.

In addition to the previous types of bonding, another type of bond consists in adsorption into any pores the spheres may have. This provides a further variation in the times at which the active substance is released.

Generally speaking, the products according to the invention contain 0.1 to 10%, more often 0.3 to 3%, in weight of the microparticles defined hereinabove, the content chosen depending on the type of polymer(s), the size of particles, their affinity for active substances and the nature and proportion of the dispersion liquid.

Concerning the active substances, the amount used is preferably the maximum amount which can be bound by the microspheres. This binding can take place through adsorption, covalent bonding or other physicochemical combinations, and/or encapsulation in the case of hollow microspheres and preferably involves most of the weight of the active substance. If no biological or medical contraindication exists, a slight excess in this or these substances can be allowed in solution or in suspension in the product's liquid. In general and depending on the case, content in active substances of the product according to the invention ranges from 0.01 to 90% in weight. This fairly wide range is justified by the fact that some active molecules, such as for example hormones, vitamins or enzymes, can be used at very low doses whereas others, such as rehydrators, anti-wrinkle or skin repair products gain from being used in fairly high doses.

The following can be given as non-limiting examples of cosmetically active substances: hydrators, preventive agents, restructurers, repairers, slimming products, antifree radical agents, non-enzymatic antiglycosylants, anti-ultraviolet agents, tanning activators, dyes, deodorants. Products covered by the invention include those in which microspheres, defined hereinabove, include substances such as dimethylsilanyl hyaluronate (D.S.H.C.), combinations of proteins with a silanol, theophylline, caffeine, tyrosine, silanol-tyrosine, camomile extract, hyaluronic acid, collagen, partially hydrolyzed elastin, theobromine, fatty acids and many others.

As therapeutic or both therapeutic and cosmetic active substances, the product according to the invention can contain vitamins, hormones, enzymes, vasodilators or vasoconstrictors, anti-inflammatory, antiseptic, cholagog, diuretic, anti-allergy, neuroleptic substances, etc. In this way, microspheres are adsorbed or bound to substances such as, for example, vitamins A, $B_1$, $B_2$, $B_6$, C, $D_3$, E, K, PP, oestrogen, androstane, Ruscus Aculeatus extract, escine, acetylsalicylic acid, glafenin, esculoside, dextropropoxyphene (HCl), piperazine, diazepam, oxazepam, promethazine, etc.

For the active substance(s) to bind to microparticles by at least one of the mechanisms described hereinabove, it is preferable for them to be in the liquid state, in solution or fine suspension, wetting the particles. This is particularly advisable when the polymer has little affinity for aqueous media, as is the case for polystyrene microspheres or microspheres in styrene-rich copolymer or when these contain little or no surfactant in their preparation. In another variant of the invention, at least one liquid secondary compound is incorporated into the product, miscible with the microsphere dispersion liquid, in order to improve contact between the active substances and the microspheres.

When the active substances bind to the latter by adsorption, the molecular weight of the secondary compound should be less than that of the active substance. Polyols, polysaccharides and mucopolysaccharides soluble or swelled up by water, as well as their silicated derivatives, lecithin and/or surfactants such as, for example, polyoxyethylene, polyoxyethylenated fatty esters of sorbital and other surfactants tolerated by the skin are all suitable for use as secondary compounds.

Some active substances can also act as secondary compounds. This is true for esters of hyaluronic acid, particularly that of dimethyl silane diol which, while acting as an energy rehydrator, can also facilitate the binding of various molecules to the microspheres. Content in the secondary compound can range from 0.1 to 80%.

Preparation of the product according to the invention can be carried out by suspending the desired amount of microspheres in a dispersion liquid, most often water, glycol or an alcohol, in a liquid also acting as an active substance or in a mixture of these two liquids. The process is carried out at room temperature with moderate stirring. The secondary compound, if it use, can be added during the course of this process.

The product obtained is preferably kept between room temperature and 1° C., as temperatures below 0° C. may cause alterations.

The invention is illustrated in a non limiting manner by the following examples.

EXAMPLE 1

Rehydrating cosmetic product in the form of conventional nanospheres 90 g of a dimethyl silane diol hyaluronate aqueous solution (19.5 g/kg i.e. 0.9 g/kg in Si) are mixed with 5 g of the microspheres of a copolymer containing 60% in weight of styrene with 40% of methyl methacrylate, having diameters ranging from 65 to 125 nm (average 95 nm) in suspension in 9.5 g of water, stirred for 10 minutes at room temperature then left for 48 hours.

It is found that the microspheres are charged with 30% of dimethylsilanediol hyaluronate.

EXAMPLE 2

Skin restructuring product based on a combination of silanol and elastin (silanol elastinate)

Microspheres of a copolymer of 4 moles of styrene per 1 mole of acrylic acid are prepared using the known process, which consists in polymerizing an aqueous emulsion of these two monomers, the emulsifying agent being Na dodecylsulfate with K persulfate as the catalyst. After polymerization, neutralization of the suspension formed, its purification by aqueous dialysis and passage over an ion-exchange resin, 10 ml of the suspension contain $10^{16}$ polymer spheres (0.55 g) having an average size of 100 nm. 10 ml of this suspension are added to 90 ml of a silanol elastinate aqueous solution at 46 g/kg (1.8 g of Si). After separation of microspheres, it is found that they have adsorbed 28% of the elastin-silanol combination, i.e. an amount containing 0.504 g of Si. The product thus obtained is used dispersed in a common cosmetic cream in three forms: at concentrations of 0.2, 2 and 5% in weight. In all cases, there is a clear restructuring effect. The elastin-Si combination is released by the microspheres in 8 to 15 hours (determined using a Frantz cell).

EXAMPLE 3

After having proceeded as in example 2, 5.5 g of the microspheres separated are dispersed in 55 ml of an emulsion composed of: 20 ml of water, 25 ml of almond oil, 8 ml of polyethylene-glycol, 1 ml of glycerine and 1 ml of polyoxyethylene-sorbitol laurate. A single daily application is enough to produce marked signs of skin repair.

EXAMPLE 4

Product containing two active substances acting at different times

The microspheres are constituted by a copolymer of 2 moles of styrene with 2 moles of butadiene and 1 mole of 2-aminoethanol methacrylate. They are prepared in the known manner, in aqueous dispersion with Na dodecylsulfate as a surfactant and K persulfate as a catalyst. After polymerization, the microspheres are neutralized, purified by aqueous dialysis and passed over an ion-exchange resin.

0.09 g of pyrrolidone carboxylic acid, which binds to the methacrylate —$NH_2$ group forming a covalent amide bond, is added to 100 ml of suspension of 4 g of these microspheres numbering about $4 \times 10^4$ (average size 96 nm). Another purification is then carried out and 6.1 g of dimethyl silanol hyaluronate, the same as in example 1, are added to the suspension and adsorbed.

The resulting suspension of 106.1 g thus contains 0.09 g of pyrrolidone carboxylic acid and 0.28 g of the Si contained in dimethyl silanol hyaluronate. Application to the skin of the product as it is, or mixed with a cosmetic cream, gel or lotion leads to release of the pyrrolidone compound in 2 to 5 hours and release of the hyaluronate compound in 10 to 17 hours. A synergetic effect of the two active substances is also observed for 2 to 5 hours, followed by a longer period of hyaluronate action only. This is seen by signs of extremely favorable rehydration.

EXAMPLE 5

Product in which microspheres carry three different active substances

The microspheres prepared in the known manner, described at the beginning of example 4, consist of a copolymer of 4 moles of styrene with 1 mole of acrylic acid.

(A)-100 g of an aqueous suspension of 5 g of microspheres are reacted with 0.126 g of theophylline, which binds to the acryl groups.

(B)-The microspheres are then given functional groups using diamine hexamethylene, after which they are treated with a 40 g/kg elastin aqueous solution. 0.3 g of elastin polypeptides thus bind to the copolymer.

(C)-The product obtained is purified and made to adsorb Ruscus Aculeatus glucosides, from an aqueous extract of this plant (Ruscus 1=33).

The final product in a 20% aqueous or oily dispersion is well-adapted to cutaneous application and has slimming, anti-water retention, as well as skin firming, effects and stimulates superficial lymphatic and venous microcirculation It is suitable for incorporation into various known cosmetics such as creams, gels, lotions, etc., preferably at concentrations ranging from 1 to 7% in weight.

The three active substances act at different times: elastin in 8 to 19 hours after application, Ruscus glucosides for 24 hours, theophylline in 2 to 8 hours.

EXAMPLE 6

Microspheres were prepared from a copolymer of 2 moles of styrene, 2 moles of vinyl acetate and 1 mole of methacrylic acid. 0.12 g of tyrosine was then bound to 100 g of a 3-g aqueous suspension of these microspheres (average size 120 nm).

The microspheres are then treated with diamine hexamethylene, thus binding an amine group. After purification, they are made to absorb two sun filters: 2-hydroxy-4-methoxy-5-benzophenone sulfonic acid and 2-ethylhexyl salicylate. Incorporated into common sun creams at a concentration of 1 to 7%, a single daily application of these products considerably improves protection against UV A and B rays by prolonging the progressive diffusion of the two filters.

EXAMPLE 7

Modification in the duration of action of two active substances by their binding to the same nanospheres by two different mechanisms.

100 g of an aqueous suspension of 5 g of nanospheres having a diameter of about 70 to 130 nm (average 100 nm) are prepared by the copolymerization of an emulsion of 4 moles of styrene and 1 mole of acrylic acid, according to the technique described in example 2. 0.126 g of theophylline, which binds to the acrylic acid groups of the copolymer by an electronic-type chemical interaction, is added to these 100 g.

To this, 0.192 g of a combination of 1 mole of theophylline with 1 mole of $CH_3Si(OH)_3$ is added, hereafter designated by the term "theophyllisilane C" and having the empirical formula $C_7H_8N_4O_2, CH_3—Si(OH)_3$. After 1 hour's stirring followed by ultra-centrifugation, it is found that 28% of the total amount of theophyllisilane used has been adsorbed by the nanospheres.

A liquid product (a-b) composed of two sets of copolymer/active substance nanospheres is thus obtained:

(a)-0.126 g of theophylline chemically bound to 5 g of nanosphere in 100 g of aqueous liquid;
(b)-0.0538 g of theophyllisilane C adsorbed by 5 g of the same nanospheres in 100 g of aqueous liquid;
the aqueous liquid contains 0.1382 g of theophyllisilane C in solution (72% of the 0.192 g used).

The liquid (a-b) is submitted to tests on an experimental model, reproducing diffusion phenomena in the skin.

The proportions of each of the active substances which may have been in contact with the skin in 3 hours is thus determined. Further, similar determinations are carried out on an aqueous solution (c-d) containing, per 100 g, 0.126 g of theophylline and 0.192 g of theophyllisilane C without any polymer particles.

Given below are the percentages of the initial amount of each of these active substances which, according to the tests mentioned hereinabove, may have been diffused into the skin from the liquid studied:

|  | (a-b) (with nanospheres) | (c-d) (without nanospheres) |
|---|---|---|
| Theophylline | 10% | 25% |
| Theophyllisilane C | 20% | 35% |

This means that the amount of active substances available to the skin is much tempered when these substances are used in the (a-b) form according to the invention: 25:10=2.5 times for theophylline and 35:20=1.75 times for theophyllisilane. Starting with the same dose, it is thus possible to obtain theophylline action at the end of a desired period of time (for example, over 3 hours) whereas theophyllisilane action has come to an end.

EXAMPLE 8

Nanospheres in water, similar to those described in the previous example, were obtained by copolymerization of 4 moles of styrene with 1 mole of methyl acrylate. They thus contained no —COOH groups likely to react with the —NH groups of theophylline.

0.126 g of theophylline and 0.192 g of theophyllisilane were added to 100 g of nanosphere aqueous suspension. The two substances were adsorbed by the nanospheres.

As above, the amount of active principal available to the skin in 3 hours was determined. The results are as follows:

20% for theophylline
22% for theophyllisilane against 10% and 20% respectively in the previous example. It can be seen that the ratio between the amounts of these two substances adsorbed by the skin has been modified by their different modes of binding to the nanospheres. Consequently, the relative durations of action of these substances are changed. The invention thus allows the chronology of action of the active substances to be modified when these substances are bound to microscopic polymer particles by different mechanisms.

EXAMPLE 9

Modification in the chronology of release of a single active substance from nanospheres through binding of the latter via two different mechanisms.

(A)-0.126 g of theophylline, which binds ionically to the —COOH groups of the copolymer, is added to 100 g of an aqueous suspension of 5 g of nanosphere of the same copolymer as that described example 7, consisting of 1 mole of acrylic acid per 4 moles of styrene. The same nanospheres are then made to adsorb 0.5 g of theophylline.

The proportion of theophylline which is available to the skin in 3 hours and in 5 hours is then determined from 100 g of an aqueous suspension of 5 g of nanosphere charged as described above.

(B)-Analogous determinations are carried out in parallel on 100 g of an aqueous suspension of 5 g of nanospheres of a similar copolymer containing —COOCH$_3$ groups instead of —COOH groups. These spheres do not bind theophylline by ionic bonds but adsorb it. They were made to adsorb 0.626 g, i.e. the same total amount as in A.

The percentages of theophylline that can thus be absorbed by the skin are

|  | in 3 hours | in 5 hours |
|---|---|---|
| A | 15% | 28% |
| B | 18% | 40% |

The result of this is that in product A, which contains both copolymer+theophylline combined to —COOH groups and adsorbed copolymer+theophylline, the chronology of action in the skin differs from that of product B containing the same amount of theophylline but in which the theophylline is only and totally adsorbed by the nanospheres.

What is claimed is:

1. Product for cutaneous application with cosmetic and/or therapeutic effects, containing one or more active substances, carried by the microspheres of a polymer, dispersed in a liquid in which this polymer is not soluble, wherein it comprises at least two kinds of microspheres-active substance sets releasing the active substances at different times, said microspheres-active substance sets being selected from the group consisting of
   (a) those wherein several active substances are bound to microspheres by at least two kinds of bonds, and
   (b) those wherein a difference in the times the active substance is released is produced by a compound carrying functional groups bound to the microspheres.

2. Product according to claim 1 wherein several active substances are bound to the microspheres by at least two kinds of bonds.

3. Product according to claim 1 wherein a difference in the times the active substance is released at is produced by a compound carrying functional groups bound to the microspheres.

4. Product according to claim 1 in which the size of the microspheres does not exceed 1000 nm.

5. Product according to claim 1 in which the microsphere dispersion liquid is water, a polyol, or an ether or ester of a cosmetically and pharmaceutically acceptable polyol.

6. Product according to claim 1 in which the polymer making up the microspheres is a polysaccharide, polyamide, polyalkylene, polyarylalkylene, polyalkylidene or polysilicone.

7. Product according to claim 1 in which content in microspheres ranges from 0.1 to 10% in weight, and content in active substance ranges from 0.01 to 90% in weight.

8. Product according to claim 1 in which the active substance(s) is a hydrator, restructurer, repairer, slimming product, anti-free radical agent, antiglycosylant, anti-ultraviolet agent, tanning activator, dye or deodorant.

9. Product according to claim 1 in which the active substance(s) is a vitamin, hormone, enzyme, vasodilator, vasoconstrictor, antiseptic, cholagog, diuretic, anti-inflammatory, anti-allergic or neuroleptic agent.

10. Product according to claim 1 containing a secondary compound, miscible with the microsphere dispersion liquid, which is a polyol, polysaccharide, mucopolysaccharide, or their silicated derivatives, and/or a surfactant.

11. Product according to claim 1 wherein it contains dimethyl silanol hyaluronate as an active substance.

12. Product according to claim 1 wherein it contains a combination of theophylline with methyl silane-triol as the active substance.

13. Product according to claim 4 in which the size of the microspheres ranges from 50 to 500 nm and the content in microspheres ranges from 0.1 to 10% in weight.

14. Process for the preparation of a product for cutaneous application with cosmetic and/or therapeutic effects, containing one or more active substances, carried by the microspheres of a polymer, dispersed in a liquid in which this polymer is not soluble, wherein it comprises at least two kinds of microspheres-active substance sets releasing the active substances at different times, said process consisting in mixing microspheres with one or more active substances in a dispersion liquid in which the microsphere polymer is not soluble, wherein one or more kinds of active substances are bound to the same microsphere by different bonds.

15. Process for the preparation of a product for cutaneous application with cosmetic and/or therapeutic effects, containing one or more active substances, carried by the microspheres of a polymer, dispersed in a liquid in which this polymer is not soluble, wherein it comprises at least two kinds of microspheres-active substance sets releasing the active substances at different times, said process consisting in mixing the microspheres with one or more active substances in a dispersion liquid in which the microsphere polymer is not soluble, wherein at least two kinds of microspheres of different polymers and/or different sizes are used, releasing a given active substance at different times, and after introduction of an active substance, the microspheres are treated with a reagent binding an intermediate functional group, which allows a second active substance to be bound whose release time is different from that of the first substance.

* * * * *